United States Patent
Hecht et al.

(10) Patent No.: US 10,932,994 B2
(45) Date of Patent: *Mar. 2, 2021

(54) TWO-COMPONENT SELF-ADHESIVE DENTAL COMPOSITION, PROCESS OF PRODUCTION AND USE THEREOF

(71) Applicant: 3M INNOVATIVE PROPERTIES COMPANY, St. Paul, MN (US)

(72) Inventors: Reinhold Hecht, Kaufering (DE); Manfred Ludsteck, Geretsried (DE); Andrea Stippschild-Boxler, Landsberg (DE); Gioacchino Raia, Turkenfeld (DE); Rainer A. Guggenberger, Herrsching (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/324,760

(22) PCT Filed: Jul. 7, 2015

(86) PCT No.: PCT/US2015/039286
§ 371 (c)(1),
(2) Date: Jan. 9, 2017

(87) PCT Pub. No.: WO2016/007453
PCT Pub. Date: Jan. 14, 2016

(65) Prior Publication Data
US 2017/0216152 A1    Aug. 3, 2017

(30) Foreign Application Priority Data
Jul. 10, 2014 (EP) .................... 14176520

(51) Int. Cl.
| A61K 6/887 | (2020.01) |
| A61K 6/62 | (2020.01) |
| A61K 6/30 | (2020.01) |
| A61K 6/80 | (2020.01) |
| C08L 33/10 | (2006.01) |
| A61K 6/61 | (2020.01) |
| A61K 6/20 | (2020.01) |
| A61K 6/54 | (2020.01) |
| A61K 6/76 | (2020.01) |
| A61K 6/77 | (2020.01) |

(52) U.S. Cl.
CPC ............ *A61K 6/61* (2020.01); *A61K 6/20* (2020.01); *A61K 6/30* (2020.01); *A61K 6/54* (2020.01); *A61K 6/76* (2020.01); *A61K 6/77* (2020.01); *A61K 6/80* (2020.01); *A61K 6/887* (2020.01)

(58) Field of Classification Search
USPC ........................ 523/118; 433/228.1
See application file for complete search history.

(56) References Cited

U.S. PATENT DOCUMENTS

| 3,729,313 A | 4/1973 | Smith |
| 3,741,769 A | 6/1973 | Smith |
| 3,808,006 A | 4/1974 | Smith |
| 4,250,053 A | 2/1981 | Smith |
| 4,259,075 A | 3/1981 | Yamauchi |
| 4,394,403 A | 7/1983 | Smith |
| 4,499,251 A | 2/1985 | Omura |
| 4,537,940 A | 8/1985 | Omura |
| 4,539,382 A | 9/1985 | Omura |
| 4,642,126 A | 2/1987 | Zador |
| 4,652,274 A | 3/1987 | Boettcher |
| 4,674,661 A | 6/1987 | Herold |
| 4,737,593 A | 4/1988 | Ellrich |
| 4,795,823 A | 1/1989 | Schmitt |
| 4,872,936 A | 10/1989 | Engelbrecht |
| 4,918,136 A | 4/1990 | Kawaguchi |
| 5,130,347 A | 7/1992 | Mitra |

(Continued)

FOREIGN PATENT DOCUMENTS

| EP | 0235826 | 9/1987 |
| EP | 0712622 | 5/1996 |

(Continued)

OTHER PUBLICATIONS

Antonucci, "New Initiator System for Dental Resins Based on Ascorbic Acid", Journal of Dental Research, 1979, vol. 58, No. 9, pp. 1887-1899.

(Continued)

*Primary Examiner* — Tae H Yoon

(57) ABSTRACT

The present invention relates to a kit of parts comprising Part A and Part B, Part A comprising: ascorbic acid, component(s) comprising an ascorbic acid moiety or derivative(s) thereof, optionally polymerizable component(s) without acidic moieties, optionally polymerizable component(s) with acidic moieties, and optionally filler(s), Part B comprising polymerizable component(s) without acidic moieties, polymerizable component(s) with acidic moieties, transition metal component(s), organic peroxide(s), and optionally filler(s), The invention is also directed to a redox initiator system comprising ascorbic acid, component(s) comprising an ascorbic acid moiety or derivative(s) thereof, transition metal component(s), preferably comprising a copper or iron ion containing salt, organic peroxide(s), preferably comprising a hydroperoxide or di-peroxide. The kit of parts and redox initiator system are particularly useful in the dental field.

12 Claims, No Drawings

(56) References Cited

U.S. PATENT DOCUMENTS

| | | | |
|---|---|---|---|
| 5,154,762 A | 10/1992 | Mitra | |
| 5,338,773 A | 8/1994 | Lu | |
| 5,501,727 A | 3/1996 | Wang | |
| 5,530,038 A | 6/1996 | Yamamoto | |
| 5,545,676 A | 8/1996 | Palazzotto | |
| 5,688,883 A * | 11/1997 | Klee | A61K 6/0017 526/141 |
| 5,918,772 A | 7/1999 | Keller | |
| 5,944,419 A | 8/1999 | Streiff | |
| 5,998,495 A | 12/1999 | Oxman | |
| 6,025,406 A | 2/2000 | Oxman | |
| 6,043,295 A | 3/2000 | Oxman | |
| 6,084,004 A | 7/2000 | Weinmann | |
| 6,105,761 A | 8/2000 | Peuker | |
| 6,187,833 B1 | 2/2001 | Oxman | |
| 6,197,212 B1 * | 3/2001 | Lindskog | A61K 6/40 252/79.4 |
| 6,444,725 B1 | 9/2002 | Trom | |
| 6,458,868 B1 | 10/2002 | Okada | |
| 6,572,693 B1 | 6/2003 | Wu | |
| 6,765,036 B2 | 7/2004 | Dede | |
| 6,899,948 B2 | 5/2005 | Zhang | |
| 6,953,535 B2 | 10/2005 | Hecht | |
| 6,998,111 B2 * | 2/2006 | Klee | A61K 6/30 424/49 |
| 2003/0176834 A1 | 9/2003 | Horth | |
| 2004/0110864 A1 | 6/2004 | Hecht | |
| 2005/0014861 A1 | 1/2005 | Qian | |
| 2005/0043490 A1 | 2/2005 | Klee | |
| 2005/0236586 A1 | 10/2005 | Hartung | |
| 2006/0187752 A1 | 8/2006 | Keller | |
| 2007/0090079 A1 | 4/2007 | Keller | |
| 2008/0207841 A1 | 8/2008 | Koers | |
| 2010/0015578 A1 | 1/2010 | Falsafi | |
| 2011/0245368 A1 | 10/2011 | Yarimizu | |
| 2012/0115978 A1 | 5/2012 | Qian | |
| 2014/0094578 A1 | 4/2014 | Tanaka et al. | |

FOREIGN PATENT DOCUMENTS

| | | |
|---|---|---|
| EP | 0783872 | 7/1997 |
| EP | 0944364 | 9/1999 |
| EP | 1051961 | 11/2000 |
| EP | 1502569 A1 * | 2/2005 |
| EP | 1759657 | 3/2007 |
| EP | 2153811 | 2/2010 |
| GB | 1316129 | 5/1973 |
| JP | 01168776 | 7/1989 |
| JP | 2004-331524 | 11/2004 |
| JP | 2006-290926 | 10/2006 |
| WO | WO 1995-22956 | 8/1995 |
| WO | WO 2003-059295 | 7/2003 |
| WO | WO 2005-016783 | 2/2005 |
| WO | WO 2007-104037 | 9/2007 |
| WO | WO 2009-061884 | 5/2009 |
| WO | WO 2009-151957 | 12/2009 |
| WO | WO 2010-123800 | 10/2010 |
| WO | WO 2011-056814 | 5/2011 |
| WO | WO 2012-150256 | 11/2012 |
| WO | WO 2015-073246 | 5/2015 |
| WO | WO 2016-007453 | 1/2016 |

OTHER PUBLICATIONS

International Search Report for PCT International Application No. PCT/US2015/039286, dated Sep. 21, 2015, 4 pages.

Belikov, V.G., "Pharmaceutical Chemistry," Second Edition, Moscow, Higher School Publishing House, 1993, Summary Translation of pp. 43-47.

Database WPI Week 200501 Thomson Scientific, Landon, GB; AN 2005-002825, XP008115310, & JP2004-331524A (Nippon Surfactant Kogyo KK) Nov. 25, 2004 (Nov. 25, 2004) abstract, 2 pages.

Database WPI Week 200681 Thomson Scientific, Landon, GB; AN 2006-792941, XP002756900, & JP2006-290926 A (Sumitomo Chem. Co Ltd.) Oct. 26, 2006 (Oct. 26, 2006) abstract, 2 pages.

Maia, "Influence of Sodium Metabisulfite and Glutathione on the Stability of Vitamin C in O/W Emulsion and Extemporaneous Aqueous Gel," International Journal of Pharmaceutics, Sep. 2006, vol. 332, No. 1-2, pp. 130-135.

International Search Report for PCT International Application No. PCT/US2016/065239, dated Feb. 17, 2017, 6 pages.

* cited by examiner

TWO-COMPONENT SELF-ADHESIVE DENTAL COMPOSITION, PROCESS OF PRODUCTION AND USE THEREOF

CROSS REFERENCE TO RELATED APPLICATIONS

This application is a National Stage Entry of International Application No. PCT/US2015/039286, filed Jul. 7, 2015, which claims the benefit of priority under 35 U.S.C. § 119(a) of EP Application No. 14176520.6 filed Jul. 10, 2014, the disclosure of which is incorporated by reference herein in its entirety.

FIELD OF THE INVENTION

The invention relates to a two-component self-adhesive composition comprising ascorbic acid or derivatives thereof, an oxidizing agent, a transition metal component. The composition may optionally contain in addition a photoinitiator system to provide dual-cure compositions. The composition can be used for various dental applications, in particular for formulating self-adhesive, self-etching dental compositions.

BACKGROUND ART

Dental composites are well known in dentistry and are widely used as restorative materials (filling composites) or as cements (resin cements) in the prosthodontic field. Generally composites are hydrophobic in nature and contain as main parts of the formulation inorganic fillers, a (meth) acrylate based resin matrix and initiators for the radical polymerization.

Redox initiating systems are well known in the dental composite area and are used in a variety of self-curing and dual-curing materials such as for example temporary crown and bridge materials, core build-up materials and resin cements.

To get adhesion to enamel and dentin, composites typically require a pre-treatment of the tooth surface by using a bonding agent or a bonding system. This may result in a rather complex and time consuming procedure. Therefore attempts were made to develop self-adhesive composites which avoid the use of an additional bonding agent/system resulting in materials which are easier and faster to use for the dentist.

In the prosthodontic area self-adhesive resin cements are well established materials in the meantime. A commercially available product is e.g. RelyX™ Unicem (3M ESPE). These materials are formulated as two-component systems. These materials cure by a sophisticated curing mechanism.

Various dental compositions curing by different mechanisms are also described in the patent literature.

EP 2 153 811 (Kerr) relates to a single-part, light-curable, self-adhering dental restorative composition comprising three different polymerizable monomers, a photoinitiator and one or more fillers.

US 2004/0110864 (Hecht et al.) relates to a self-adhesive composition comprising one or more mono- or polyfunctional ethylenically unsaturated acidic compounds, one or more mono- or polyfunctional ethylenically unsaturated non-acidic compounds, filler, initiators and additives.

U.S. Pat. No. 6,953,535 (Hecht et al.) relates to a redox initiator system which allows dental formulations to be cured in acidic medium by way of a free-radical polymerization, the redox initiator system comprising a barbituric acid or thiobarbituric acid derivative, peroxodisulfate, a sulfinic acid compound and a copper compound.

U.S. Pat. No. 5,154,762 (Mitra et al.) describes a dental cement containing water, acid-reactive filler, water-miscible acidic polymer, an ethylenically-unsaturated moiety, photoinitiator, water-soluble reducing agent and water-soluble oxidizing agent. The cement is said to have three curing modes, namely an acid-filler ionic reaction, a photoinitiated crosslinking reaction and a redox-initiated crosslinking reaction.

U.S. Pat. No. 4,918,136 (Kawaguchi et al.) describes an adhesive composition comprising a certain monomer mixture, filler, a polymerization initiator and a certain amount of ascorbic acid or a derivative thereof.

U.S. Pat. No. 5,501,727 (Wang et al.) relates to a curable dental composition comprising an ethylenically unsaturated moiety, an oxidizing agent and a metal complexed ascorbic acid. The incorporation of metal complexed ascorbic acid provides a curable composition that exhibits improved color stability.

U.S. Pat. No. 5,338,773 (Lu et al.) describes a dental cement composition useful as dental luting cement, liner, base and restorative. The cement is said to have superior adhesion to tooth without separately acid etching dentin or enamel. The cement can be provided as a powder/liquid composition, wherein the powder contains a strontium aluminofluorosilicate glass powder, benzoyl peroxide, ascorbyl palmitate and cupricacetyl acetonate.

J. M. Antonucci et al describes new initiator systems for dental resins. The initiator systems suggested contain peresters and hydroperoxides as oxidants, natural reducing agents such as ascorbic acid as accelerators in combination with redo4x metal systems (Journal of Dental Research, Vol. 58, No. 9, September 1979, pages 1887-1899).

SUMMARY

It would be desirable to have a two-component, preferably dual-curable composition showing good adhesion not only to enamel but also dentin surfaces combined with good mechanical and, if possible, aesthetic properties.

In particular, it would be desirable to have a two-component composition showing good adhesion to enamel and dentin surfaces combined with good mechanical properties in the self-cure mode.

This object can be solved by a kit of parts as described in the present text comprising a Part A and a Part B,
Part A (i.e. Catalyst Part) Comprising
  optionally filler(s),
  optionally polymerizable component(s) without acidic moieties,
  optionally polymerizable component(s) with acidic moieties,
  ascorbic acid, component(s) comprising an ascorbic acid moiety or derivative(s) thereof,
Part B (i.e. Base Part) Comprising
  optionally filler(s),
  polymerizable component(s) without acidic moieties,
  polymerizable component(s) with acidic moieties,
  transition metal component(s),
  organic peroxide(s), preferably selected from hydroperoxide(s) and di-peroxide(s), each of the components being as described in the present text.

In another embodiment (e.g. powder/liquid formulation) Part A comprises
filler(s)
ascorbic acid, component(s) comprising an ascorbic acid moiety or derivative(s) thereof, and Part B comprises
polymerizable component(s) without acidic moieties,
polymerizable component(s) with acidic moieties,
transition metal component(s),
organic peroxide(s), preferably selected from hydroperoxide(s) and di-peroxide(s), each of the components being as described in the present text.

A further embodiment of the invention is directed to a process of producing the composition as described in any of the preceding claims comprising the steps of mixing and/or kneading.

A further embodiment of the invention is directed to the use of an initiator system comprising ascorbic acid or derivative(s) thereof, transition metal component(s) and organic peroxide(s) as described in the present text for curing a dental composition comprising polymerizable component(s) with acidic moieties.

In particular the invention is directed to the use of an initiator system comprising ascorbic acid or derivative(s) thereof, transition metal component(s) comprising a copper or iron ion containing salt, organic peroxide(s) in particular hydroperoxides or di-peroxide and optionally a sensitizing and a further reducing agent for curing a dental composition comprising polymerizable component(s) with acidic moieties.

A further embodiment of the invention is directed to a dental composition obtained or obtainable by mixing the compositions contained in Part A and Part B of the kit of parts described in the present text and curing the resulting mixture.

A further embodiment of the invention is directed to a method of using the kit of parts described in the present text or the composition obtained by mixing the compositions contained in Part A and Part B of the kit of parts described in the present text, the method comprising the steps of applying the composition to a surface and curing the composition by a self-cure mechanism or optionally by applying radiation.

Other embodiments, features and advantages of the present invention will be apparent from the following detailed description, drawings, and claims.

Unless defined differently, for this description the following terms shall have the given meaning: "One component" means that all of the components mentioned are present in the composition during storage and use. That is, the composition to be applied or used is not prepared by mixing different parts of the composition before use. In contrast to one-component compositions, those compositions are often referred to as two-component compositions (e.g. being formulated as powder/liquid, liquid/liquid or paste/paste compositions).

"Two component" means that the kit of parts or system is provided in parts separated from each other before use. In contrast to a "two component system" a "one component system" is provided as one part only.

A "dental composition" or a "composition for dental use" or a "composition to be used in the dental field" is any composition which can be used in the dental field. In this respect the composition should be not detrimental to the patients' health and thus be free of hazardous and toxic components being able to migrate out of the composition. Examples of dental compositions include permanent and temporary crown and bridge materials, artificial crowns, anterior or posterior filling materials, adhesives, mill blanks, lab materials, luting agents and orthodontic devices. Dental compositions are typically hardenable compositions, which can be hardened at ambient conditions, including a temperature range from about 15 to 50° C. or from about 20 to 40° C. within a time frame of about 30 min or 20 min or 10 min.

Higher temperatures are not recommended as they might cause pain to the patient and may be detrimental to the patient's health. Dental compositions are typically provided to the practitioner in comparable small volumes, that is volumes in the range from about 0.1 to about 100 ml or from about 0.5 to about 50 ml or from about 1 to about 30 ml. Thus, the storage volume of useful packaging devices is within these ranges.

The term "compound" or "component" is a chemical substance which has a particular molecular identity or is made of a mixture of such substances, e.g., polymeric substances.

A "monomer" is any chemical substance which can be characterized by a chemical formula, bearing polymerizable groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth)acryloxy" group is a shorthand term referring to either an acryloxy group (i. e., $CH_2$=CH—C(O)—O—) and/or a methacryloxy group (i. e., $CH_2$=C($CH_3$)—C(O)—O—). Similarly, (meth)acrylate is a shorthand term referring to "acrylate" and/or "methacrylate."

A "hardenable component or material" or "polymerizable component" is any component which can be cured or solidified e.g. by heating to cause polymerization, chemical crosslinking, radiation-induced polymerization or crosslinking by using a redox initiator. A hardenable component may contain only one, two, three or more polymerizable groups. Typical examples of polymerizable groups include unsaturated carbon groups, such as a vinyl group being present i.a. in a (meth)acrylate group.

An "ethylenically unsaturated acidic compound" is meant to include monomers, oligomers, and polymers having ethylenic unsaturation and acid and/or acid-precursor functionality. Acidic precursor functionalities include, e.g. anhydrides, acid halides and pyrophosphates. The acidic group preferably comprises one or more carboxylic acid residues, such as —COOH or —CO—O—CO—, phosphoric acid residues, such as —O—P(O)(OH)OH, phosphonic acid residues such as C—P(O)(OH)OH, sulfonic acid residues, such as —$SO_3$H or sulfinic acid residues such as —$SO_2$H.

A "filler" contains all fillers being present in the hardenable composition. Only one type of filler or a mixture of different fillers can be used.

By "paste" is meant a soft, viscous mass of solids (i.e. particles) dispersed in a liquid.

A "particle" means a substance being a solid having a shape which can be geometrically determined. The shape can be regular or irregular. Particles can typically be analysed with respect to e.g. grain size and grain size distribution.

A "powder" is characterized by containing only solid components in particle form.

A "non-surface treated filler" is a filler having a surface which has not been exposed to reactive substances resulting in a modification of the surface of the filler to make the filler more compatible or reactive with other components of the composition.

An "adhesive" or "dental adhesive" refers to a composition used as a pre-treatment on a dental structure (e. g., a tooth) to adhere a "dental material" (e. g., "restorative" an orthodontic appliance (e. g., bracket), or an "orthodontic adhesive") to a dental surface. An "orthodontic adhesive" refers to a composition used to adhere an orthodontic appliance to a dental (e. g., tooth) surface. Generally, the dental surface is pre-treated, e. g., by etching, priming, and/or applying an adhesive to enhance the adhesion of the "orthodontic adhesive" to the dental surface.

A "dental surface" or "tooth surface" refers to the surface of tooth structures (e. g., enamel, dentin, and cementum) and bone.

A "self-etching" composition refers to a composition which bonds to a dental surface without pre-treating the dental surface with an etchant. Preferably, a self-etching composition can also function as a self-primer wherein no separate etchant or primer is used.

A "self-adhesive" composition refers to a composition that is capable of bonding to a dental surface without pre-treating the dental surface with a primer or bonding agent. Preferably, a self-adhesive composition is also a self-etching composition wherein no separate etchant is used.

A "self-curing composition" means a composition which cures by a redox-reaction without application of radiation.

An "untreated" dental surface refers to a tooth or bone surface that has not been treated with an etchant, primer, or bonding agent prior to application of a self-etching adhesive or a self-adhesive composition.

An "unetched" dental surface refers to a tooth or bone surface that has not been treated with an etchant prior to application of a self-etching adhesive or a self-adhesive composition of the present invention.

An "etchant" refers to an acidic composition that is capable of fully or partially solubilizing (i. e., etching) a dental surface. The etching effect can be visible to the naked human eye and/or instrumentally detectably (e. g., by light microscopy). Typically, an etchant is applied to the dental structure surface for a period of about 10 to 30 seconds.

A composition can be classified as "storage stable", if it remains stable over a considerable long period of time (at least about 4 weeks to more than about 12 months under ambient conditions). A storage stable composition does typically not show decomposition of the components contained therein or premature polymerization over time. Moreover, the features intended to be achieved by the composition shall not diminish more than desired.

A "nano-sized filler" is a filler, the individual particles thereof have a size in the region of nanometers, e.g. an average particle diameter of less than about 200 nm. Useful examples are given in U.S. Pat. Nos. 6,899,948 and 6,572,693, the content of which especially with regard to nano-sized silica particles is herein incorporated by reference.

An "initiator system" shall include those components of the dental composition being able to start or initiate the curing process of the hardenable components, also described herein as "curing the hardenable components."

"Curing," "hardening," and "setting reaction" are used interchangeably and refer to a reaction wherein physical properties such as viscosity and hardness of a composition change (e.g., increase) over time due to a chemical reaction between the individual components.

A composition is characterized as "dual-curing" if it contains one or more initiator systems allowing the composition to be cured either by radiation or without radiation by a redox reaction, i.e. by a self-cure mechanism.

"Radiation curable" shall mean that the component (or composition, as the case may be) can be cured by applying radiation, preferably electromagnetic radiation with a wavelength in the visible light spectrum under ambient conditions and within a reasonable time frame (e.g. within about 60, 30 or 10 seconds).

A "derivative" is a chemical compound showing a chemical structure closely related to the corresponding reference compound and containing all featured structural elements of the corresponding reference compound but having small modifications like bearing additional chemical groups like e.g. $CH_3$, Br, Cl, or F or not bearing chemical groups like e.g. $CH_3$ in comparison to the corresponding reference compound. That is, a derivative is a structural analogue of the reference compound. A derivative of a chemical compound is a compound comprising the chemical structure of said chemical compound. Another example of a derivative is a salt formed by a chemical compound e.g. in an acid-base reaction.

The following examples might illustrate this: tetramethyl bis-phenol A bearing four additional methyl groups with respect to the reference compound bis-phenol A, and bis-phenol F not bearing two additional methyl groups with respect to the reference compound bis-phenol A are derivatives of bis-phenol A within the meaning of this definition.

The term "visible light" is used to refer to light having a wavelength of about 400 to about 800 nanometers (nm).

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar. In the dental and orthodontic field ambient conditions are reasonably understood as a pressure of about 950 to about 1050 mbar, temperature of about 15 to about 40° C. and relative humidity of about 20 to about 80%.

A composition is "essentially or substantially free of" a certain component within the meaning of the invention, if the composition does not contain said component as an essential feature. Thus, said component is not willfully added to the composition either as such or in combination with other components or ingredient of other components. A composition being essentially free of a certain component usually contains the component in an amount of less than about 1 wt.-% or less than about 0.1 wt.-% or less than about 0.01 wt.-% with respect to the whole composition. Ideally, the composition or solution does not contain the said component at all. However, sometimes the presence of a small amount of the said component is not avoidable e.g. due to impurities.

"Comprise" includes the terms "contain", "essentially consists of" and "consists of". As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.). Unless otherwise indicated, all numbers expressing quantities of ingredients, measurement of physical properties such as described below and so forth used in the specification and claims are to be understood as being modified in all instances by the term "about."

DETAILED DESCRIPTION OF THE INVENTION

Redox initiators described in the prior art are typically systems based on peroxide-amine, peroxide/hydroperoxide-thiourea, persulfate-ascorbic acid and barbituric acid-peroxide-copper-chloride (so called Bredereck system).

Most of these systems, however, do not work under acidic conditions and may lead to insufficient cure and therefore cannot be used for the formulation of self-adhesive compositions or self-curing adhesives.

In addition, redox initiator systems often do not generate mechanical properties comparable to photoinitiated systems. These drawbacks are avoided with systems and compositions described in the present text. These materials cure efficiently even under acidic conditions, thus allowing the formulation of self-adhesive compositions with improved adhesion to dentin and enamel and mechanical properties comparable to those which can be obtained when using a photoinitiator system.

In contrast to the redox initiator systems of the state of the art, the redox initiator system described in the present text allows the hardening of unsaturated components such as e.g. (meth)acrylate(s) by free radical polymerization under acidic conditions. It provides an efficient cure as indicated by very good mechanical properties (e.g. flexural strength), but also promotes adhesion to enamel and dentin. Therefore this initiator system is quite useful for the development of self-curing, self-adhesive composites including self-adhesive and self-curing filling and luting materials.

Thus, the composition and kit of parts described in the present text is suitable to solve at least one of the above mentioned objectives, e.g. providing a two-component, self-etching, self-adhesive, optionally dual curing dental composition with good adhesive properties especially with respect to dentin surfaces.

The composition and kit of parts described in the present text is also suitable to bond to high strength ceramics such as zirconia or alumina, glass ceramics, composite materials and precious (e.g. Au) and non-precious metals (e.g. Ti) and the respective alloys.

It was found that the composition and kit of parts described in the present text is able to bond to the surfaces of these materials even without a chemical pre-treatment step (such as treatment with silanes, zirconia and/or metal primers).

However, if desired a chemical pre-treatment step can be applied if an even higher bond strength is required.

Further, surprisingly it was found that the formulation described in the present text results in a sufficiently stable composition, that is, in compositions contained in the individual parts which do not cure during a reasonable storage period unless mixing of the individual parts.

The compositions contained in Part A or Part B of the kit of parts described in the present text can be either in paste, liquid or powder form. Thus, the kit of parts can be provided as a paste/paste, powder/liquid or liquid/liquid formulation.

The composition contained in Part A can typically be characterized by at least one, more or all of the following features:
 being a paste, liquid or powder,
 pH value upon contact with water 3 to 12 or 3 to 8.

The composition contained in Part B can typically be characterized by at least one, more or all of the following features:
 being a paste or a liquid
 pH value upon contact with water below 7 or below 6 or below 5 or below 4.

Besides sufficient storage stability, the composition obtained by mixing the compositions contained in Part A and Part B of the kit of parts described in the present text is self-etching and/or self-adhesive. That is, the composition adheres to dental surfaces without a pre-treatment using e.g. an etchant and/or a bonding system.

Besides the feature of self-adhesiveness the composition typically has overall good mechanical properties.

The composition obtained by mixing the compositions contained in Part A and Part B of the kit of parts described in the present text can typically be characterized by at least one or more or all of the following features before hardening:
 pH value if brought in contact with water: below 7 immediately after mixing
 viscosity: from about 0.01 to about 1,000 Pa*s measured at 23° C.

The composition obtained by mixing the compositions contained in Part A and Part B of the kit of parts described in the present text can typically be characterized by at least one or more or all of the following features after curing:
 Flexural strength determined according to ISO 4049:2009 at least 50 MPa or at least 70 MPa or at least 90 MPa;
 Adhesion to dentin determined according to wire loop adhesion (see experimental part): at least 5 MPa or at least 7 MPa or at least 9 MPa;
 Adhesion to enamel determined according to wire loop adhesion (see experimental part): at least 5 MPa or at least 7 MPa or at least 9 MPa.

Depending on the intended use, the viscosity of the composition is typically adjusted.

If the composition is used as dental fissure sealant or dental flowable, suitable viscosities include e.g. from 1 to 150 Pa*s or from 10 to 120 Pa*s (23° C.; shear rate: 100 l/s).

If desired, the viscosity can be determined as described in the Example section.

The composition can be cured in an acceptable time frame by the redox initiator system contained therein, e.g., within less than 300 seconds (s) or less than 180 s or less than 120 s at a temperature of 37° C.

The pH value of the individual pastes or of the mixed composition can be determined by using wet pH sensitive paper.

The composition described in the present text is provided as a kit of parts containing a base part and a catalyst part. Besides those parts typically an instruction of use is included containing hints how to use the kit of parts and apply the composition obtained by combining the compositions contained in the individual parts.

The composition obtained by combining Part A and Part B contained in the individual parts comprises
 optionally filler(s),
 polymerizable component(s) without acidic moieties,
 ascorbic acid, component(s) comprising an ascorbic acid moiety or derivative(s) thereof,
 polymerizable component(s) with acidic moieties,
 transition metal component(s),
 organic peroxide(s),
 optionally a photoinitiator system, and
 optionally additive(s).

Part A and Part B of the kit of parts described in the present text may contain filler(s). One or more fillers may be present, if desired. The nature and structure of the filler(s) is not particularly limited unless the intended purpose cannot be achieved.

Adding a filler is beneficial e.g. for adjusting the rheological properties like the viscosity. The content of the filler also typically influences the physical properties of the composition after hardening, like hardness or flexural strength.

The size of the filler particles should be such that a homogeneous mixture with the hardenable component forming the resin matrix can be obtained—

The mean particle size of the filler may be in the range from 5 nm to 100 μm.

If desired, the measurement of the particle size of the filler particles can be done with a TEM (transmission electron microscopy) method, whereby a population is analyzed to obtain an average particle diameter.

A preferred method for measuring the particle diameter can be described as follows: Samples approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 Kv. A population size of about 50-100 particles can be measured and an average diameter is determined. The filler(s) typically comprise non acid reactive fillers. A non-acid reactive filler is a filler which does not undergo an acid/base reaction with an acid.

Useful non-acid reactive fillers include fumed silica, fillers based on non-acid reactive fluoroaluminosilicate glasses, quartz, ground glasses, non water soluble fluorides such as $CaF_2$, silica gels such as silicic acid, in particular pyrogenic silicic acid and granulates thereof, cristobalite, calcium silicate, zirconium silicate, zeolites, including the molecular sieves.

Suitable fumed silicas include for example, products sold under the tradename Aerosil™ series OX-50, -130, -150, and -200, Aerosil R8200 available from Degussa AG (Hanau, Germany), CAB-O-SIL™ M5 available from Cabot Corp (Tuscola, Ill.), and HDK types e.g. HDK-H2000, HDK H15, HDK H18, HDK H20 and HDK H30 available from Wacker.

Filler(s) which can also be used and which provide radioopacity to the dental materials described in the present text include heavy metal oxide(s) and fluoride(s). As used herein, "radiopacity" describes the ability of a hardened dental material to be distinguished from tooth structure using standard dental X-ray equipment in the conventional manner. Radiopacity in a dental material is advantageous in certain instances where X-rays are used to diagnose a dental condition. For example, a radiopaque material would allow the detection of secondary caries that may have formed in the tooth tissue surrounding a filling. The desired degree of radiopacity can be varied, depending upon the particular application and the expectations of the practitioner evaluating the X-ray film.

Oxides or fluorides of heavy metals having an atomic number greater than about 28 can be preferred. The heavy metal oxide or fluoride should be chosen such that undesirable colors or shading are not imparted to the hardened resin in which it is dispersed. For example, iron and cobalt would not be favoured, as they impart dark and contrasting colors to the neutral tooth color of the dental material. More preferably, the heavy metal oxide or fluoride is an oxide or fluoride of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Suitable metal fluorides are e.g. Yttriumtrifluoride and Ytterbiumtrifluoride. Most preferably, the oxides and fluorides of heavy metals having an atomic number greater than 30, but less than 72 are optionally included in the materials of the invention. Particularly preferred radiopacifying metal oxides include lanthanum oxide, zirconium oxide, yttrium oxide, ytterbium oxide, barium oxide, strontium oxide, cerium oxide, and combinations thereof. The heavy metal oxide particles may be aggregated. If so, it is preferred that the aggregated particles are less than about 200 nm, and more preferably are less than about 90 nm in average diameter.

Other suitable fillers to increase radiopacity are salts of barium and strontium especially strontium sulphate and barium sulphate.

Filler(s) which can also be used include nano-sized fillers such as nano-sized silica.

Suitable nano-sized particles typically have a mean particle size in the range of about 5 to about 80 nm.

Preferred nano-sized silicas are commercially available from Nalco Chemical Co. (Naperville, Ill.) under the product designation NALCO COLLOIDAL SILICAS (for example, preferred silica particles can be obtained from using NALCO products 1040, 1042, 1050, 1060, 2327 and 2329), Nissan Chemical America Company, Houston, Tex. (for example, SNOWTEX-ZL, -OL, -O, -N, -C, -20L, -40, and -50); Admatechs Co., Ltd., Japan (for example, SX009-MIE, SX009-MIF, SC1050-MJM, and SC1050-MLV); Grace GmbH & Co. KG, Worms, Germany (for example, those available under the product designation LUDOX, e.g., P-W50, P-W30, P-X30, P-T40 and P-T40AS); Akzo Nobel Chemicals GmbH, Leverkusen, Germany (for example, those available under the product designation LEVASIL, e.g., 50/50%, 100/45%, 200/30%, 200A/30%, 200/40%, 200A/40%, 300/30% and 500/15%), and Bayer MaterialScience AG, Leverkusen, Germany (for example, those available under the product designation DISPERCOLL S, e.g., 5005, 4510, 4020 and 3030).

Surface-treating the nano-sized silica particles before loading into the dental material can provide a more stable dispersion in the resin. Preferably, the surface-treatment stabilizes the nano-sized particles so that the particles will be well dispersed in the hardenable resin and results in a substantially homogeneous composition. Furthermore, it is preferred that the silica be modified over at least a portion of its surface with a surface treatment agent so that the stabilized particle can copolymerize or otherwise react with the hardenable resin during curing.

Thus, the silica particles as well as other suitable non acid-reactive fillers can be treated with a resin-compatibilizing surface treatment agent.

Particularly preferred surface treatment or surface modifying agents include silane treatment agents capable of polymerizing with a resin. Preferred silane treatment agent include gamma-methacryloxylpropyltrimethoxysilane, available commercially under the trade designation A-174, available commercially from Witco OSi Specialties (Danbury, Conn.) and gamma-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, alkyl or aryl polyethers, alkyl, hydroxy alkyl, hydroxy aryl, or amino alkyl functional silanes.

Besides an inorganic material the filler(s) can also be based on an organic material. Examples of suitable organic filler particles include filled or unfilled pulverized polycarbonates, poly(meth)acrylates, polyepoxides, and the like.

If Part A of the kit of parts described in the present text does not contain polymerizable component(s) with acidic moieties acid-reactive fillers can be contained in Part A, if desired.

Examples of acid-reactive fillers which may be present in Part A of the kit of parts include acid-reactive fluoroaluminosilicate glasses (sometimes also referred to as GIC glasses), basic fillers like the oxides, hydroxides and carbonates of calcium, magnesium, lanthanum, strontium, zinc or mixtures thereof. These fillers can be also surface treated.

Suitable acid-reactive fillers are also described in e.g. in GB 1,316,129 and WO 95/22956 (Wang et al.).

The amount of filler to be used in the filler matrix usually depends on the purpose for which the composition should be used.

If present, the filler is typically present in the following amounts. The amount is given with respect to the weight of the whole composition.

Lower limit: at least 1 wt.-% or at least 5 wt.-% or at least 10 wt.-%.

Upper limit: utmost 90 wt.-% or utmost 80 wt.-% or utmost 70 wt.-%.

Range: from 1 wt.-% to 90 wt.-% or from 5 wt.-% to 80 wt.-% or from 10 wt.-% to 70 wt.-%.

If the amount of filler is too low, mechanical strength of the cured composition might be too low for the intended application.

If the amount of filler is too high, undesirable handling properties like too high viscosity, or poor wetting and penetration of a dental hard tissue might occur.

Part B and optionally Part A of the kit of parts described in the present text contain polymerizable component(s) without acidic moiety(s).

One or more polymerizable component(s) without acidic moiety(s) may be present, if desired. The nature and structure of those components is not particularly limited unless the intended purpose cannot be achieved.

Polymerizable component(s) without acidic moiety(s) contained in Part A of the kit of parts can be same or different from the polymerizable component(s) without acidic moiety(s) contained in Part B of the kit of parts.

The polymerizable component(s) without acidic moiety(s) is typically a free-radically polymerizable material, including ethylenically unsaturated monomer, monomers or oligomers or polymers.

Suitable polymerizable component(s) without acidic moiety(s) can be characterized by the following formula:

$$A_n\text{-}B\text{-}A_m$$

with A being an ethylenically unsaturated group, such as a (meth)acryl moiety,

B being selected from (i) linear or branched C1 to C12 alkyl, optionally substituted with other functional groups (e.g. halogenides (including Cl, Br, I), OH or mixtures thereof) (ii) C6 to C12 aryl, optionally substituted with other functional groups (e.g. halogenides, OH or mixtures thereof), or (iii) organic group having 4 to 20 carbon atoms bonded to one another by one or more ether, thioether, ester, thioester, thiocarbonyl, amide, urethane, carbonyl and/or sulfonyl linkages, m, n being independently selected from 0, 1, 2, 3, 4, 5 or 6 with the proviso that n+m is greater 0, that is that at least one A group is present.

Such polymerizable materials include mono-, di- or polyacrylates and methacrylates such as methyl acrylate, methyl methacrylate, ethyl (meth)acrylate, isopropyl (meth)acrylate, n-hexyl (meth)acrylate, stearyl (meth)acrylate, allyl (meth)acrylate, glycerol di(meth)acrylate, the diurethane dimethacrylate called UDMA (mixture of isomers, e.g. Röhm Plex 6661-0) being the reaction product of 2-hydroxyethyl methacrylate (HEMA) and 2,2,4-trimethylhexamethylene diisocyanate (TMDI), glycerol tri(meth)acrylate, ethyleneglycol di(meth)acrylate, diethyleneglycol di(meth)acrylate, triethyleneglycol di(meth)acrylate, 1,3-propanediol diacrylate, 1,3-propanediol dimethacrylate, trimethylolpropane tri(meth)acrylate, 1,2,4-butanetriol tri(meth)acrylate, 1,4-cyclohexanediol di(meth)acrylate, pentaerythritol tri(meth)acrylate, pentaerythritol tetraacrylate, pentaerythritol tetramethacrylate, sorbitol hexa(meth)acrylate, bis[1-(2-(meth)acryloxy)]-p-ethoxyphenyldimethylmethane, bis[1-(3-methacryloxy-2-hydroxy)]-p-propoxyphenyldimethylmethane (BisGMA), bis[1-(3-acryloxy-2-hydroxy)]-p-propoxyphenyldimethylmethane and trishydroxyethyl-isocyanurate trimethacrylate; the bis-acrylates and bis-methacrylates of polyethylene glycols of molecular weight 200-500, copolymerizable mixtures of acrylated monomers (see e.g. U.S. Pat. No. 4,652,274), and acrylated oligomers (see e.g. U.S. Pat. No. 4,642,126); and vinyl compounds such as styrene, diallyl phthalate, divinyl succinate, divinyl adipate and divinylphthalate; polyfunctional (meth)acrylates comprising urethane, urea or amide groups. Mixtures of two or more of these free radically polymerizable materials can be used if desired.

Further polymerizable components which may be present include di(meth)acrylates of ethoxylated bis-phenol A, for example 2,2'-bis(4-(meth)acryl-oxytetraethoxyphenyl)propanes, urethane (meth)acrylates and (meth)acrylamides. The monomers used can furthermore be esters of [alpha]-cyanoacrylic acid, crotonic acid, cinnamic acid and sorbic acid.

It is also possible to use the methacrylic esters mentioned in EP 0 235 826, such as bis[3[4]-methacryl-oxymethyl-8 (9)-tricyclo[5.2.1.0$^{2,6}$]decylmethyl triglycolate. Suitable are also 2,2-bis-4-(3-methacryloxy-2-hydroxypropoxy)phenylpropane (Bis-GMA), 2,2-bis-4-(3-methacryloxypropoxy) phenylpropane, 7,7,9-trimethyl-4,13-dioxo-3,14-dioxa-5, 12-diazahexadecane-1,16-dioxy dimethacrylate (UDMA), urethane (meth)acrylates and di(meth)acrylates of bishydroxymethyltricyclo-(5.2.1.0$^{2,6}$)decane.

These ethylenically unsaturated monomers can be employed in the dental composition(s) either alone or in combination with the other ethylenically unsaturated monomers. In addition or besides those components, other hardenable components which can be added include oligomeric or polymeric compounds, such as polyester (meth)acrylates, polyether (meth)acrylates, polycarbonate (meth)acrylates and polyurethane (meth)acrylates. The molecular weight of these compounds is typically less than 20,000 g/mol, particularly less than 15,000 g/mol and in particular less than 10,000 g/mol.

Polymerizable monomers comprising a hydroxyl moiety and/or a 1,3-diketo moiety can also be added. Suitable compounds include 2-hydroxyethyl (meth)acrylate (HEMA), 2- or 3-hydroxypropyl (meth)acrylate, 4-hydroxybutyl (meth)acrylate, 5-hydroxypentyl (meth)acrylate, 6-hydroxyhexyl (meth)acrylate, 10-hydroxydecyl (meth)acrylate, dialkylene glycol mono(meth)acrylate, for example, diethylene glycol mono(meth)acrylate, triethylene glycol mono(meth)acrylate, tetraethylene glycol mono(meth)acrylate, polyethylene glycol mono(meth)acrylate, dipropylene glycol mono(meth)acrylate, polypropylene glycol mono (meth)acrylate, and further 1,2- or 1,3- and 2,3-dihydroxypropyl (meth)acrylate, 2-hydroxypropyl-1,3-di(meth)acrylate, 3-hydroxypropyl-1,2-di(meth)acrylate, N-(meth)acryloyl-1,2-dihydroxypropylamine, N-(meth)acryloyl-1,3-dihydroxypropylamine, adducts of phenol and glycidyl (meth)acrylate, for example, 1-phenoxy-2-hydroxypropyl (meth)acrylate, 1-naphthoxy-2-hydroxypropyl (meth)acrylate, bisphenol A diglycidyl (meth)acrylate and the like, 2-hydroxyethyl (meth)acrylate, 2-hydroxypropyl (meth) acrylate and 2,3-dihydroxypropyl (meth)acrylate are particularly preferable.

An example of a polymerizable component with 1,3-diketo group is acetoacetoxy ethylmethacrylate (AAEMA). If desired, mixtures of one or more of these components can be used. Adding these components may be used to adjust the rheological properties or to influence mechanical properties.

The polymerizable component(s) without acidic moiety(s) is typically present in the following amounts with respect to the weight of the whole composition:
Lower limit: at least 5 wt.-% or at least 10 wt.-% or at least 20 wt.-%;
Upper limit: utmost 65 wt.-% or utmost 55 wt.-% or utmost 45 wt.-%;
Range: from 5 wt.-% to about 65 wt.-% or from 10 wt.-% to 55 wt.-% or from 20 wt.-% to 45 wt.-%.

Part A of the kit of parts described in the present text contains ascorbic acid or one or more derivatives of ascorbic acid including salts and esters of ascorbic acid.

Suitable salts include the alkali metal and earth alkali metal salts like Na, K, and mixtures thereof.

Esters of ascorbic acid include those which are formed by reacting one of the hydroxyl functions of ascorbic acid with a carboxylic acid, in particular the C2 to C30 carboxylic acid.

Suitable examples of C2 to C30 carboxylic acids include the fatty acids, like caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid and docosahexaenoic acid.

In particular preferred are ascorbic acid, ascorbyl palmitate, ascorbyl stearate, and mixtures thereof.

The ascorbic acid or derivative thereof is typically present in the following amounts with respect to the weight of the whole composition:
Lower limit: at least 0.01 wt.-% or at least 0.05 wt.-% or at least 0.1 wt.-%;
Upper limit: utmost 5 wt.-% or utmost 3 wt.-% or utmost 1 wt.-%;
Range: from 0.01 wt.-% to 5 wt.-% or from 0.05 wt.-% to 3 wt.-% or from 0.1 wt.-% to 1 wt.-%.

If the amount of ascorbic acid or derivative(s) thereof is too high, the setting time of the composition may be too fast.

If the amount of ascorbic acid or derivative(s) thereof is too low, the setting time of the composition may be too slow.

Part B of the kit of parts described in the present text contain polymerizable component(s) with acidic moiety(s).

If desired, polymerizable component(s) with acidic moiety(s) may also be contained in Part A of the kit of parts.

One or more polymerizable component(s) with acidic moiety(s) may be present, if desired. The nature and structure of those components is not particularly limited unless the intended purpose cannot be achieved.

The hardenable components with acid moiety can typically be represented by the following formula

$A_n\text{-}B\text{---}C_m$ with A being an ethylenically unsaturated group, such as a (meth)acryl moiety,
B being a spacer group, such as (i) linear or branched C1 to C12 alkyl, optionally substituted with other functional groups (e.g. halogenides (including Cl, Br, I), OH or mixtures thereof) (ii) C6 to C12 aryl, optionally substituted with other functional groups (e.g. halogenides, OH or mixtures thereof), (iii) organic group having 4 to 20 carbon atoms bonded to one another by one or more ether, thioether, ester, thioester, thiocarbonyl, amide, urethane, carbonyl and/or sulfonyl linkages, and
C being an acidic group, or precursor of an acidic group such as acid anhydride,
m, n being independently selected from 1, 2, 3, 4, 5 or 6,
wherein the acidic group comprises one or more carboxylic acid residues, such as —COOH or —CO—O—CO—, phosphoric acid residues, such as —O—P(O)(OH)OH, phosphonic acid residues, such as C—P(O)(OH)(OH), sulphonic acid residues, such as —SO$_3$H or sulfinic acid residues such as —SO$_2$H.

Examples of hardenable components with acid moiety include, but are not limited to glycerol phosphate mono (meth)acrylate, glycerol phosphate di(meth)acrylate, hydroxyethyl (meth)acrylate (e.g., HEMA) phosphate, bis ((meth)acryloxyethyl) phosphate, (meth)acryloxypropyl phosphate, bis((meth)acryloxypropyl) phosphate, bis((meth) acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylate, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly (meth)acrylated polyboric acid, and the like. Derivatives of these hardenable components bearing an acid moiety that can readily react e.g. with water to form the specific examples mentioned above, like acid halides or anhydrides are also contemplated.

Also monomers, oligomers, and polymers of unsaturated carboxylic acids such as (meth)acrylic acids, aromatic (meth)acrylated acids (e.g., methacrylated trimellitic acids), and anhydrides thereof can be used.

Some of these compounds can be obtained, e.g., as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. If desired, mixtures of such compounds can be used.

Using (meth)acrylate functionalized polyalkenoic acids is often preferred as those components were found to be useful to improve properties like adhesion to hard dental tissue, formation of a homogeneous layer, viscosity, or moisture tolerance.

According to one embodiment, the composition contains (meth)acrylate functionalized polyalkenoic acids, for example, AA:ITA:IEM (copolymer of acrylic acid:itaconic acid with pendent methacrylates).

These components can be made by reacting e.g. an AA:ITA copolymer with 2-isocyanatoethyl methacrylate to convert a portion of the acid groups of the copolymer to pendent methacrylate groups. Processes for the production of these components are described, e.g., in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and EP 0 712 622 A1 (Tokuyama Corp.) and EP 1 051 961 A1 (Kuraray Co., Ltd.).

The polymerizable component(s) with acidic moiety(s) is typically present in the following amounts:
Lower limit: at least 2 wt.-% or at least 3 wt.-% or at least 4 wt.-%;
Upper limit: utmost 50 wt.-% or utmost 40 wt.-% or utmost 30 wt.-%;
Range: from 2 wt.-% to about 50 wt.-% or from about 3 wt.-% to about 40 wt.-% or from about 4 wt.-% to about 30 wt.-%;
wt.-% with respect to the weight of the whole composition obtained by combining the compositions contained in Part A and Part B of the kit of parts.

Part B of the kit of parts described in the present text contains one or more transition metal components.

Suitable transition metal component(s) include organic and/or inorganic salt(s) from titanium, vanadium, chromium, manganese, iron, cobalt, nickel, copper and/or zinc, with copper and iron being sometimes preferred.

Useful salts include acetate(s), chloride(s), sulphate(s), benzoate(s), acetylacetonate(s), naphthenate(s), carboxylate(s), bis(1-phenylpentan-1,3-dione) complexes, salicylate(s), complexes with ethylenediaminetetraacetic acid of either of the transition metals and mixtures thereof.

According to one embodiment, the transition metal component is in an oxidation stage, which allows the component to be reduced. Useful oxidation stages include +2, +3, +4, +5, +6 and +7, as applicable.

Copper component(s) are sometimes preferred. The oxidation stage of copper in the copper component(s) is preferably +1 or +2.

Typical examples of copper component(s) which can be used include salts and complexes of copper including copper acetate, copper chloride, copper benzoate, copper acetylacetonate, copper naphthenate, copper carboxylates, copper bis(1-phenylpentan-1,3-dione) complex (copper proceto-nate), copper salicylate, complexes of copper with thiourea, ethylenediaminetetraacetic acid and/or mixtures thereof.

The copper compounds can be used in hydrated form or free of water. Especially preferred is copper acetate.

The amount of transition metal component which can be used is not particularly limited.

The transition metal salt should be used in an amount sufficient to achieve the intended purpose.

The transition metal component(s) is typically present in the following amounts:
Lower limit: at least 0.00001 wt.-% or at least 0.0001 wt.-% or at least 0.001 wt.-%;
Upper limit: utmost 3 wt.-% or utmost 2 wt.-% or utmost 1.5 wt.-%;
Range: from 0.00001 wt.-% to 3 wt.-% or from 0.0001 wt.-% to 2 wt.-% or from 0.001 wt.-% to 1.5 wt.-%
wt.-% with respect to the weight of the whole composition obtained by combining the compositions contained in Part A and Part B of the kit of parts. If the amount of transition metal component used is too high, the setting time of the composition may be too fast.

If the amount of transition metal component used is too low, the setting time of the composition may be too slow and adhesion may be reduced-Generally all organic peroxide(s) can be used, if suitable to achieve the desired result.

In contrast to inorganic peroxides, organic peroxide(s) do not comprise metals or metal ions. Thus, organic peroxides typically only comprise C, O, H and optionally halogens (e.g. F, Cl, Br). Organic peroxides which can be used include di-peroxide(s) and hydroperoxides.

According to one embodiment, the organic peroxide is a di-peroxide, preferably a di-peroxide comprising the moiety $R_1$—O—O—$R_2$—O—O—$R_3$, with $R_1$ and $R_3$ being independently selected from H, alkyl (e.g. C1 to C6), branched alkyl (e.g. C1 to C6), cycloalkyl (e.g. C5 to C10), alkylaryl (e.g. C7 to C12) or aryl (e.g. C6 to C10) and $R_2$ being selected from alkyl (e.g. (C1 to C6) or branched alkyl (e.g. C1 to C6).

According to another embodiment, the organic peroxide is a hydroperoxide, in particular a hydroperoxide comprising the structural moiety

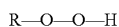

R—O—O—H with R being (e.g. C1 to C20) alkyl, (e.g. C3 to C20) branched alkyl, (e.g. C6 to C12) cycloalkyl, (e.g. C7 to C20) alkylaryl or (e.g. C6 to C12) aryl.

Examples of suitable organic hydroperoxides include t-butyl hydroperoxide, t-amyl hydroperoxide, p-diisopropylbenzene hydroperoxide, cumene hydroperoxide, pinane hydroperoxide, p-methane hydroperoxide and 1,1,3,3-tetramethylbutyl hydroperoxide and mixtures thereof.

Examples of suitable organic diperoxides include 2,2-Di-(tert-butylperoxy)-butane and 2,5-Dimethyl-2,5-di-(tert-butylperoxy)-hexane and mixtures thereof.

Other peroxide which are often described in the literature are ketone peroxide(s), diacyl peroxide(s), dialkyl peroxide(s), peroxyketal(s), peroxyester(s) and peroxydicarbonate(s).

Examples of ketone peroxides include methyl ethyl ketone peroxide, methyl isobutyl ketone peroxide, methyl cyclohexanone peroxide, and cyclohexanone peroxide.

Examples of peroxyesters include -cumylperoxyneodecanoate, t-butyl peroxypivarate, t-butyl peroxyneodecanoate, 2,2,4-trimethylpentylperoxy-2-ethyl hexanoate, t-amylperoxy-2-ethyl hexanoate, t-butylperoxy-2-ethyl hexanoate, di-t-butylperoxy isophthalate, di-t-butylperoxy hexahydroterephthalate, t-butylperoxy-3,3,5-trimethylhexanoate, t-butylperoxy acetate, t-butylperoxy benzoate and t-butylperoxymaleic acid.

Examples of peroxidicarbonates include di-3-methoxy peroxidicarbonate, di-2-ethylhexyl peroxydicarbonate, bis(4-t-butylcyclohexyl)peroxidicarbonate, diisopropyl-1-peroxydicarbonate, di-n-propyl peroxidicarbonate, di-2-ethoxyethyl-peroxidicarbonate, and diallyl peroxidicarbonate.

Examples of diacyl peroxides include acetyl peroxide, benzoyl peroxide, decanoyl peroxide, 3,3,5-trimethylhexanoyl peroxide, 2,4-dichlorobenzoyl peroxide and lauroylperoxide.

Examples of dialkyl peroxides include di-t-butyl peroxide, dicumylperoxide, t-butylcumyl peroxide, 2,5-dimethyl-2,5-di(t-butylperpoxy)hexane, 1,3-bis(t-butylperoxyisopropyl)benzene and 2,5-dimethyl-2,5-di(t-butylperoxy)-3-hexane.

Examples of peroxyketals include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane and 4,4-bis(t-butylperoxy)valeric acid-n-butylester.

The organic peroxide(s) is typically present in the following amounts:

Lower limit: at least 0.01 wt.-% or at least 0.05 wt.-% or at least 0.1 wt.-%;
Upper limit: utmost 5 wt.-% or utmost 4 wt.-% or utmost 3 wt.-%;
Range: from 0.01 wt.-% to 5 wt.-% or from 0.05 wt.-% to 4 wt.-% or from 0.1 wt.-% to 3 wt.-%;
wt.-% with respect to the weight of the whole composition.

If the amount of the organic peroxide(s) is too high, the setting time of the composition may be too fast.

If the amount of the organic peroxide(s) is too low, the setting time of the composition may be too slow.

Besides the described redox-initiator system comprising ascorbic acid or derivative(s) thereof, transition metal component(s) and organic peroxide(s), the kit of parts described in the present text may also comprise in addition a photoinitiator system.

The nature of the optional photoinitiator system is not particularly limited unless the intended purpose is not negatively affected.

By incorporating a photoinitiator system a composition is obtained which can be characterized as "dual curing", that is, it contains a redox-initiator system which is suitable to harden the composition without radiation ("dark-curing or self-curing") and a photoinitiator system is suitable to harden the composition upon the application of radiation ("light curing").

Suitable photoinitiator systems for free radical polymerization are generally known to the person skilled in the art dealing with dental materials. Typical photoinitiator systems comprise a combination of a sensitizing agent and a reducing agent.

As the sensitizing agent, those which can polymerize the polymerizable monomer(s) by the action of a visible light having a wavelength of from 390 nm to 830 nm are preferred.

Examples thereof include camphorquinone, benzil, diacetyl, benzyl dimethyl ketal, benzyl diethyl ketal, benzyl di(2-methoxyethyl) ketal, 4,4,'-dimethylbenzyl dimethyl ketal, anthraquinone, 1-chloroanthraquinone, 2-chloroanthraquinone, 1,2-benzantraquinone, 1-hydroxyanthraquinone, 1-methylanthraquinone, 2-ethylanthraquinone, 1-bromoanthraquinone, thioxanthone, 2-isopropyl thioxanthone, 2-nitrothioxanthone, 2-methyl thioxanthone, 2,4-dimethyl thioxanthone, 2,4-diethyl thioxanthone, 2,4-diisopropyl thioxanthone, 2-chloro-7-trifluoromethyl thioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl)ketone, 4,4,'-bisdiethylaminobenzophenone.

As the reducing agent, tertiary amines and the like are generally used. Suitable examples of the tertiary amines include N,N-dimethyl-p-toluidine, N,N-dimethylaminoethyl methacrylate, triethanolamine, methyl 4-dimethylaminobenzoate, ethyl 4-dimethylaminobenzoate, and isoamyl 4-dimethylaminobenzoate. As other reducing agents, sodium sulfinate derivatives and organometallic compounds can also be used. These compounds may be used singly or in admixture.

Moreover, ternary photopolymerization initiating systems consisting of a sensitizer, an electron donor and an onium salt as described in U.S. Pat. Nos. 6,187,833, 6,025,406, 6,043,295, 5,998,495, 6,084,004, 5,545,676 and WO 2009151957 and U.S. patent application Ser. No. 10/050, 218 can be used and are included herein by reference.

In the ternary photoinitiator system, the first component is an iodonium salt, i.e., a diaryliodonium salt. The iodonium salt is preferably soluble in the monomer and shelf-stable (i e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. Nos. 3,729,313, 3,741,769, 3,808,006, 4,250,053 and 4,394,403, the iodonium salt disclosures of which are incorporated herein by reference. The iodonium salt can be a simple salt (e.g., containing an anion such as $Cl^-$, $Br^-$, $I^-$ or $C_4H_5 SO_3^-$) or a metal complex salt (e.g., containing $SbF_5OH^-$ or $AsF_6^-$). Mixtures of iodonium salts can be used if desired. Preferred iodonium salts include diphenyliodonium salts such as diphenyliodonium chloride, diphenyliodonium hexafluorophosphate and diphenyliodonium tetrafluoroborate.

The second component in a ternary photoinitiator system is a sensitizer. The sensitizer desirably is soluble in the monomer, and is capable of light absorption somewhere within the range of wavelengths of greater than 400 to 1200 nanometers, more preferably greater than 400 to 700 nanometers and most preferably greater than 400 to about 600 nanometers. The sensitizer may also be capable of sensitizing 2-methyl-4,6-bis(trichloromethyl)-s-triazine, using the test procedure described in U.S. Pat. No. 3,729,313, which is incorporated herein by reference. Preferably, in addition to passing this test, a sensitizer is also selected based in part upon shelf stability considerations. Accordingly, selection of a particular sensitizer may depend to some extent upon the particular monomer, oligomer or polymer, iodonium salt and donor chosen.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring deep cure (e.g., cure of highly-filled composites), it is preferred to employ sensitizers having an extinction coefficient below about 1000, more preferably below about 100, at the desired wavelength of irradiation for photopolymerization. Alternatively, dyes that exhibit reduction in light absorption at the excitation wavelength upon irradiation can be used.

For example, a preferred class of ketone sensitizers has the formula: ACO(X)$_b$ B, where X is CO or CR$^5$R$^6$, where R$^5$ and R$^6$ can be the same or different, and can be hydrogen, alkyl, alkaryl or aralkyl, b is zero or one, and A and B different and can be substituted (having one or more non-interfering substituents) can be the same or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone and the like.

The third component of a ternary initiator system is a donor. Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676, which is incorporated herein by reference.

Alternatively, free-radical initiators useful in the invention include the class of acylphosphine oxides and bisacylphosphine oxides.

Suitable acylphosphine oxides can be described by the general formula

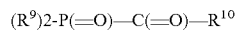

(R$^9$)2-P(=O)—C(=O)—R$^{10}$ wherein each R$^9$ individually can be a hydrocarbyl group such as alkyl, cycloalkyl, aryl, and aralkyl, any of which can be substituted with a halo-, alkyl- or alkoxy-group, or the two R$^9$ groups can be joined to form a ring along with the phosphorous atom, and wherein R$^{10}$ is a hydrocarbyl group, an S-, O-, or N-containing five- or six-membered heterocyclic group, or a —Z—C(=O)—P(=O)—(R$^9$)$_2$ group, wherein Z represents a divalent hydrocarbyl group such as alkylene or phenylene having from 2 to 6 carbon atoms.

Preferred acylphosphine oxides are those in which the R$^9$ and R$^{10}$ groups are phenyl or lower alkyl- or lower alkoxy-substituted phenyl. By "lower alkyl" and "lower alkoxy" is meant such groups having from 1 to 4 carbon atoms. Examples can also be found e.g. in U.S. Pat. No. 4,737,593.

Suitable bisacylphosphine oxides can be described by the general formula

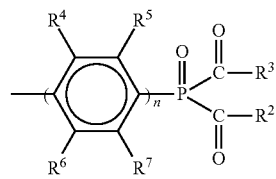

wherein n is 1 or 2, and R$^4$, R$^5$, R$^6$ and R$^7$ are H, C1-4 alkyl, C1-4 alkoxyl, F, Cl or Br; R$^2$ and R$^3$, which are the same or different, stand for a cyclohexyl, cyclopentyl, phenyl, naphthyl, or biphenylyl radical, a cyclopentyl, cyclohexyl, phenyl, naphthyl, or biphenylyl radical substituted by F, Cl, Br, I, C1-4 alkyl and/or C1-4 alkoxyl, or an S or N-containing 5-membered or 6-membered heterocyclic ring; or R$^2$ and R$^3$ are joined to form a ring containing from 4 to 10 carbon atoms and being optionally substituted by 1 to 6 C1-4 alkyl radicals.

Further examples include: bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-ethoxyphenylphosphine oxide, bis-(2,6-dichlorobenzoyl)-4-biphenylylphosphine oxide, bis-(2,6-dichlorobenzoyl)-4-propylphenylphosphine oxide, bis-(2,6-dichlorobenzoyl)-2-naphthylphosphine oxide, bis-(2,6-dichlorobenzoyl)-1-napthylphosphine oxide, bis-(2,6-dichlorobenzoyl)-4-chlorophenylphosphine oxide, bis-(2,6-dichlorobenzoyl)-2,4-dimethoxyphenylphosphine oxide, bis-(2,6-dichlorobenzoyl)decylphosphine oxide, bis-(2,6-dichlorobenzoyl)-4-octylphenylphosphine oxide, bis-(2,6-dimethoxybenzoyl)-2,5-dimethylphenylphosphine oxide, bis-(2,6-dimethoxybenzoyl)phenylphosphine oxide, bis-(2,4,6-trimethylbenzoyl)-2,5-dimethylphenylphosphine oxide, bis-(2,6-dichloro-3,4,5-tri-methoxybenzoyl)-2,5-dimethylphenylphosphine oxide, bis-(2,6-dichloro-3,4,5-trimethoxy-benzoyl)-4-ethoxyphenylphosphine oxide, bis-(2-methyl-1-naphthoyl)-2,5-dimethylphenylphosphine oxide, bis-(2-methyl-1-naphthoyl)phenylphosphine oxide, bis-(2-methyl-1-naphthoyl)-4-biphenylylphosphine oxide, bis-(2-methyl-1-naphthoyl)-4-ethoxyphenylphosphine oxide, bis-(2-methyl-1-naphthoyl)-2-naphthylphosphine oxide, bis-(2-methyl-1-naphthoyl)-4-propylphenylphosphine oxide, bis-(2-methyl-1-naphthoyl)-2,5-dimethylphosphine oxide, bis-(2-methoxy-1-naphthoyl)-4-ethoxyphenylphosphine oxide, bis-(2-methoxy-1-naphthoyl)-4-biphenylylphosphine oxide, bis-(2-methoxy-1-naphthoyl)-2-naphthylphosphine oxide, and bis-(2-chloro-1-naphthoyl)-2,5-dimethylphenylphosphine oxide.

The acylphosphine oxide bis(2,4,6-trimethylbenzoyl)phenyl phosphine oxide (IRGACURE™ 819, Ciba Specialty Chemicals, Tarrytown, N.Y.) is sometimes preferred.

Tertiary amine reducing agents may be used in combination with an acylphosphine oxide. Illustrative tertiary amines useful in the invention include ethyl 4-(N,N-dimethylamino)benzoate and N,N-dimethylaminoethyl methacrylate.

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl- 1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis(η5-2,4-cyclopentadien-1-yl)-bis (2,6-difluoro-3-(1H-pyrrol-1-yl)phenyl) titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

The sensitizing agent and reducing agent are typically present together in one part of the kit of parts described in the present text. Alternatively the components of a photoinitiator system can be spread between Part A and Part B. For stability reasons, it can be preferred, if the photoinitiator system is contained in Part A, i.e. the part containing the ascorbic acid or derivative(s) thereof.

Besides the above mentioned components, the composition described in the present text or parts of the kit of parts may further contain one, two or more additives. Additives of adjuvants which can be used include accelerators, inhibitors or retarders, absorbers, stabilizers, pigments, dyes, surface tension depressants and wetting aids, antioxidants, and other ingredients well known to those skilled in the art. The amounts and types of each ingredient in the composition should be adjusted to provide the desired physical and handling properties before and after polymerization.

Examples of dyes or pigments, which can be used include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual colouring of the dental compositions.

Examples of photobleachable colorants which can be present include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photobleachable colorants can be found in U.S. Pat. No. 6,444,725. The colour of the compositions of the invention may be additionally imparted by a sensitizing compound.

Examples of fluoride release agents which can be present include naturally occurring or synthetic fluoride minerals. These fluoride sources can optionally be treated with surface treatment agents.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, phenothiazine, and HALS (hindered amine light stabilizers). Such adjuvants may optionally comprise reactive moiety so that they will be copolymerized with the resin.

Further additives, which can be added, include retarders, (such as 1,2-diphenylethylene), plasticizers (including polyethylene glycol derivatives, polypropylene glycols, low-molecular-weight polyesters, dibutyl, dioctyl, dinonyl and diphenyl phthalate, di(isononyl adipate), tricresyl phosphate, paraffin oils, glycerol triacetate, bisphenol A diacetate, ethoxylated bisphenol A diacetate, and silicone oils), flavorants, anti-microbials, fragrance, agents that impart fluorescence and/or opalescence.

In order to increase the flexibility of the dental material, it is also possible to add soluble organic polymers including polyvinyl acetate, and copolymers thereof.

There is no absolute need for these adjuvants or additives to be present, so adjuvants or additives might not be present at all. However, if they are present they are typically present in an amount which is not detrimental to the intended purpose.

If present, the additive(s) is (are) typically present in the following amounts. The amount is given with respect to the weight of the whole composition.

Lower limit: at least 0.01 wt.-% or at least 0.05 wt.-% or at least 0.1 wt.-%;
Upper limit: utmost 15 wt.-% or utmost 10 wt.-% or utmost 5 wt.-%;
Range: from 0.01 wt.-% to 15 wt.-% or from 0.05 wt.-% to 10 wt.-% or from 0.1 wt.-% to 5 wt.-%.

According to a further embodiment, the kit of parts described in the present text comprises:

Part A Comprising
Filler(s),
Polymerizable component(s) with acidic moieties (optional)
Polymerizable component(s) without acidic moieties,
Ascorbic acid, component(s) comprising an ascorbic acid moiety or derivative(s) thereof,
Sensitizing agent(s) comprising an alpha di-keto moiety,
Reducing agent(s) comprising a tertiary amine moiety, Part B Comprising
Filler(s),
Polymerizable component(s) without acidic moieties,
Polymerizable component(s) with acidic moieties,
Transition metal component(s) comprising a copper or iron ions containing salts,
Organic peroxide(s) having the structure R—O—O—H as described in the text above, the composition obtained immediately after mixing of Part A and Part B having a pH value below 7 upon contact with water,
neither Part A nor Part B comprising components selected from component(s) comprising a sulfinate moiety,
component(s) comprising a barbituric acid moiety,
component(s) comprising a thiobarbituric acid moiety,
component(s) comprising an aryl borate moiety,
component(s) comprising a thiourea moiety,
the compositions contained in Part A and Part B forming upon combination a self-adhesive, self-etching, self-curing or optionally dual-curing dental composition.

The composition described in the present text can be obtained by combining (including mixing and kneading) the individual components of the composition, preferably under "safe light" conditions.

Suitable inert solvents may be employed if desired when providing the mixture. Any solvent may be used which does not react appreciably with the components of the inventive compositions.

Examples of solvents include, but are not limited to linear, branched or cyclic, saturated or unsaturated alcohols, ketones, esters or mixtures of two or more of said type of solvents with 2 to 10 C atoms. Preferred alcoholic solvents include methanol, ethanol, iso-propanol and n-propanol.

Other suitable organic solvents are THF, acetone, methylethyl ketone, cyclohexanol, toluene, alkanes and acetic acid alkyl esters, in particular acetic acid ethyl ester.

It is possible to use the above-mentioned solvents alone or as a mixture of two or more of any of these solvents, if the solvent mixtures do not impair the adhesive properties to such an extent that the desired result cannot be obtained.

The compositions described in the present text are particularly well adapted for use as a wide variety of dental materials, which may be filled or unfilled.

Such dental materials include direct aesthetic restorative materials (e.g., anterior and posterior restoratives), adhesives for oral hard tissues, sealants, cavity liners, orthodontic bracket adhesives for use with any type of bracket (such as metal, plastic and ceramic), crown and bridge cements, and the like.

These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth. The term "composite" as used herein in the context of a dental material refers to a filled dental material. The term "restorative" as used herein refers to a dental composite that is polymerized after it is disposed adjacent to a tooth. The term "prosthesis" as used herein refers to a composite that is shaped and polymerized for its final use (e.g., as a crown, bridge, veneer, inlay, onlay or the like) before it is disposed adjacent to a tooth. The term "sealant" as used herein refers to a lightly filled dental composite or to an unfilled dental material that is cured after it is disposed adjacent to a tooth.

Possible uses of the composition described in the present text in the dental field include the use as anterior or posterior filling, adhesive, cavity liner, flowable, cement, coating composition, root canal filling, root canal sealant or core build-up material.

The dental composition described in the present text can be applied to the surface of hard dental tissue and cured by a self cure mechanism or optionally by applying radiation.

A typical application process for the composition described in the present text typically includes the following steps in the desired order:
  providing a composition obtained by combining (e.g. mixing) the compositions contained in Part A and Part B of the kit of parts described in the present text,
  placing that composition in contact with hard dental tissue, especially the surface thereof,
  curing that composition by a self-cure mechanism or optionally, by applying radiation (e.g. visible light) to the composition for a period of time sufficient to initiate the polymerisation process (e.g. about 5 to about 20 s).

As the composition is self-adhesive, no prior etching step or use of a bonding/primer is needed. Thus, the composition described in the present text can be used as a self-adhesive, self-etching cement.

However, if desired, applying a prior etching step or use of an adhesive/primer system is possible, as well. Thus, the composition described in the present text can be used in an adhesive cementation procedure (i.e. cement composition in combination with an adhesive), too.

Surprisingly it was found that the physical/mechanical properties of the cured composition described in the present text are not negatively affected, if e.g. the surface of a tooth is treated with a self-etching adhesive before the composition described in the present text is applied. If, however, a prior etching and/or adhesive bonding step is conducted, the bond strength of the cured composition described in the present text is typically further improved.

Thus, according to one embodiment, the application process for the composition described in the present text includes the following steps:
  applying a self-etching adhesive to the surface of hard dental tissue,
  optionally curing the self-etching adhesive,
  providing a composition obtained by combining (e.g. mixing) the compositions contained in Part A and Part B of the kit of parts described in the present text,
  placing that composition in contact with the hard dental tissue having been treated with the curable self-etching adhesive,
  curing that composition by a self-cure mechanism or optionally, by applying radiation (e.g. visible light) to the composition for a period of time sufficient to initiate the polymerisation process (e.g. about 5 to about 20 s).

Self-etching adhesives typically have a lower viscosity compared to dental cements. Suitable self-etching adhesives which can be used include e.g. Scotchbond™ Universal Adhesive or Adper™ Prompt™ L-Pop (both from 3M ESPE). A self-etching adhesive is an adhesive which does not require a separate etching step (e.g. by phosphoric acid).

According to another embodiment (total etch procedure), the application process for the composition described in the present text includes the following steps:
  etching of the surface of hard dental tissue (e.g. by using phosphoric acid) and rinsing with water,
  applying an adhesive to the surface of the etched hard dental tissue,
  optionally curing the adhesive,
  providing a composition obtained by combining (e.g. mixing) the compositions contained in Part A and Part B of the kit of parts described in the present text,
  placing the composition in contact with the hard dental tissue having been treated with the adhesive,
  curing the composition by a self-cure mechanism or optionally, by applying radiation (e.g. visible light) to the composition for a period of time sufficient to initiate the polymerization process (e.g. 5 to about 20 s), Adhesives typically have a lower viscosity compared to dental cements. Suitable total etch adhesives include e.g. Adper™ Scotchbond™ 1XT and Adper™ Scotchbond™ Multipurpose (both from 3M ESPE).

Suitable tools for applying radiation include dental curing lights. Suitable dental curing lights are described e.g. in US 2005/0236586. The content of this document is herewith incorporated by reference. Suitable dental curing lights are also commercially available e.g. under the trade names Elipar™ S10 (3M ESPE).

The kit of parts described in the present text is typically stored in a dual-chamber container or cartridge and is mixed before use. Depending on the formulation, various containers can be used.

Cartridges which can be used are described e.g. in US 2007/0090079 or U.S. Pat. No. 5,918,772, the disclosure of which is incorporated by reference. Some of the cartridges which can be used are commercially available e.g. from SulzerMixpac AG (Switzerland). Static mixing tips which can be used are described e.g. in US 2006/0187752 or in U.S. Pat. No. 5,944,419, the disclosure of which is incorporated by reference. Mixing tips which can be used are commercially available from SulzerMixpac AG (Switzerland).

The container may comprise a housing having a front end with a nozzle and a rear end and at least one piston movable in the housing.

Alternatively, but less preferred, paste/paste compositions described in the present text can be provided in two individual syringes and the individual pastes can be handmixed prior to use.

Low viscous compositions can be stored in a vial or bottle. Suitable vials are described e.g. in EP 0 944 364 B1 and WO 2011/056814 A1. The content of these documents with respect to the description of the vial or bottle is herewith incorporated by reference.

Low viscous composition may also be stored in a container formed by two sheets, interconnected by hot sealing and cooperating to form a compartment for receiving the liquid and a pocket for receiving a brush. These kind of devices are described e.g. in U.S. Pat. No. 6,105,761.

It is also possible to store the composition in a dental mixing capsule. Examples of dental mixing capsules include those described e.g. in EP 1 759 657 (3M), U.S. Pat. No. 4,674,661 (Herold), EP 0 783 872 (Voco), or US 2003/0176834 (Horth et al.). The content of these references are herewith incorporated by reference.

If desired, a part of the redox-initiator system described in the present text may also be located on an application device (e.g. brush). Upon use, the brush containing the respective redox-initiator component (e.g. reducing agent) is brought in contact with the remaining parts of the redox-initiator system, which may be contained in a blister, bottle or vial. This application form is in particular useful for low viscous compositions, e.g. dental adhesive compositions.

The volume of the container is typically in the range from about 0.1 to about 100 ml or from about 0.5 to about 50 ml or from about 1 to about 30 ml.

Depending on the formulation chosen, the compositions described in the present text can be provided as liquid/liquid, paste/paste, or liquid/powder formulations.

The invention is also directed to an initiator system comprising
component(s) comprising an ascorbic acid moiety or derivative(s) thereof,
a copper or iron ion containing salt,
organic peroxide(s), preferably comprising a hydroperoxide or di-peroxide moiety bearing component.

The invention is also directed to an initiator system comprising
component(s) comprising an ascorbic acid moiety or derivative(s) thereof,
transition metal component(s), preferably comprising a copper or iron ion containing salt,
a hydroperoxide or di-peroxide moiety bearing component.

The invention is also directed to an initiator system comprising
component(s) comprising an ascorbic acid moiety or derivative(s) thereof,
a copper or iron ion containing salt,
a hydroperoxide moiety or di-peroxide bearing component.
optionally a sensitizing agent and a reducing agent.

Such initiator systems are in particular useful for curing acidic compositions and in particular for formulating self-adhesive, self-etching dental compositions or self-curing adhesives.

Thus, the invention is also directed to the use of an initiator system as described in the present text for curing a composition comprising polymerizable component(s) with acidic moieties as described in the present text or to a composition comprising polymerizable component(s) with acidic moieties and an initiator system as described in the present text.

The invention is also directed to a process of hardening a dental composition comprising polymerizable component(s) with acidic moieties as described in the present text by using a redox initiator system as described in the present text.

The invention is also directed to a composition comprising polymerizable component(s) with acidic moieties, more than 20 wt.-% filler and an initiator system as described in the present text. Such a composition is in particular useful as dental filling or composite material.

The invention is also directed to a composition comprising polymerizable component(s) with acidic moieties, less than 15 wt.-% filler and an initiator system as described in the present text. Such a composition is in particular useful as a dental adhesive material.

The individual components of the initiator system are as described in the present text for the kit of parts.

The inventive composition does typically not contain components comprising a sulfinate moiety (especially sulfinate salts such as sodium toluene sulfinate), barbituric acid moiety, thiobarbituric acid moiety, an aryl borate moiety, a thiourea moiety, or mixtures thereof.

Thus, according to a further embodiment the inventive composition may not comprise either of the following components or combinations thereof:
component comprising a barbituric or thiobarbituric acid moiety,
component comprising an aryl borate moiety,
component comprising a sulfinate moiety,
a thiourea moiety,
component comprising an aryl borate moiety and component comprising a sulfinate moiety.

According to one embodiment the composition described in the present text does not comprise Bis-GMA in an amount of more than 1 or 3 or 5 wt.-% with respect to the weight of the whole composition. According to one embodiment the composition described in the present text is essentially free of Bis-GMA.

According to a further embodiment, the composition described in the present text does not comprise HEMA in an amount of more than 1 or 3 or 5 wt.-% with respect to the weight of the whole composition. According to one embodiment the composition described in the present text is essentially free of HEMA.

Unavoidable traces of these components might be present (e.g. due to impurities in the raw materials used). However, those components are typically not willfully added in an amount to participate in the curing reaction.

Examples

Unless otherwise indicated, all parts and percentages are on a weight basis, all water is de-ionized water, and all molecular weights are weight average molecular weight.

Moreover, unless otherwise indicated all experiments were conducted at ambient conditions (23° C.; 1013 mbar). Moreover, nearly all process steps are conducted under an atmosphere of dry air:

Measurements

Viscosity

If desired, the viscosity can be measured using a Physica MCR 301 Rheometer (Anton Paar, Graz, Austria) with a cone/plate geometry CP25-1 under controlled shear rate at 23° C. The diameter is 25 mm, the cone angle 1°, and the separation between the cone tip and the plate 49 μm. The shear rate is ramped down logarithmically from 100 s$^{-1}$ to 0.001 s$^{-1}$.

Flexural Strength and E-Modulus

This measurement was conducted according to ISO 4049: 2000.

Adhesion (Wire Loop Method)

This measurement was conducted as follows:

As substrates, bovine teeth were embedded in cold cure epoxy resin and ground to expose dentin or enamel with a 320 grit SiC paper. Finally the surface of each tooth was rinsed with water and gently air-dried.

The testing material was filled into the testing mold (diameter: 5 mm), directly fixed on the tooth surface and self-cured at 36° C. and 100% relative humidity or light-cured for 20 sec.

Bonded specimens were tested after 24 hr storage in tab water (light-cured), respectively 100% relative humidity (self-cured) at 36° C. in a universal testing machine (Zwick) with a crosshead speed of 2 mm/min. To shear off the test buttons a looped orthodontic wire was used.

To determine the flexural strength and adhesion to enamel and dentin, the respective Catalyst Paste and Base Paste were mixed in a 1:1 ratio (by volume). The setting of the mixed pastes in the self-cure mode took place within about 10 min (at 28° C.).

Abbreviations

Sr-glass: strontium glass filler, 4.6% silane treated
HDK H 2000: fumed silica
Aerosil R805: fumed silica
UDMA: urethanedimethacrylate (Plex 6661); 7,7,9-(resp. 7,9,9-)Trimethyl-4,13-dioxo-3,14-dioxa-5,12-diaza-hexadecane-1,16-dioxy dimethacrylate (mixture of isomers)
GDMA: glycerol dimethacrylate
MHP: methacryloylhexaphosphate
GDP: glycerine dimethacrylate phosphate
MPDADM: methoxypropyl-diethanolamine dimethacrylate
CC: camphorquinone
EDMAB: ethyl-4-dimethylaminobenzoate
AA: ascorbic acid
AP: ascorbyl palmitate
Thiourea: N,N-diphenylthiourea
Na-TSS: sodium toluenesulfinate
CHP: cumene hydroperoxide
AHP: amyl hydroperoxide
TBPB: tert. Butylperoxybenzoate
DBPO: dibenzoylperoxide
BHT: 2,6-ditert.butyl-4-methylphenol

TABLE 1

Composition of Catalyst Pastes of Examples 1-6 (Inventive) and Example 6a (Comparative)

| Component | Ex. 1 wt.-% | Ex. 2 wt.-% | Ex. 3 wt.-% | Ex. 4 wt.-% | Ex. 5 wt.-% | Ex. 6 wt.-% | Ex. 6a wt.-% |
|---|---|---|---|---|---|---|---|
| Sr-glass | 62.59 | 62.72 | 61.9 | 62.59 | 61.9 | 62.72 | 61.90 |
| Aerosil | — | — | — | — | — | — | 1.49 |
| HDK H-2000 | 1.5 | 1.5 | 1.5 | 1.5 | 1.5 | 1.5 | — |
| UDMA | 12.68 | 12.85 | 13.00 | 12.68 | 13.00 | 13.00 | 13.0 |
| GDMA | 19.87 | 20.14 | 20.19 | 19.96 | 20.19 | 20.17 | 20.19 |
| MHP | 1.95 | 1.98 | 2.00 | 1.95 | 2.00 | 2.0 | 2.0 |
| MPDADM | 1.0 | — | 1.0 | 1.0 | 1.0 | — | 1.0 |
| CC | 0.1 | 0.1 | 0.1 | — | 0.1 | 0.1 | 0.1 |
| EDMAB | — | — | — | — | — | 0.2 | — |
| AA | 0.3 | — | 0.3 | 0.3 | 0.3 | 0.3 | 0.3 |
| AP | — | 0.7 | — | — | — | — | — |
| BHT | 0.01 | 0.01 | 0.01 | 0.02 | 0.01 | 0.01 | 0.01 |

TABLE 2

Composition of Base Pastes of Examples 1-6 (Inventive) and Example 6a (Comparative)

| Component | Ex. 1 wt.-% | Ex. 2 wt.-% | Ex. 3 wt.-% | Ex. 4 wt.-% | Ex. 5 wt.-% | Ex. 6 wt.-% | Ex. 6a wt.-% |
|---|---|---|---|---|---|---|---|
| Sr-glass | 59.43 | 59.43 | 59.43 | 59.43 | 59.43 | 59.43 | 59.43 |
| HDK H-2000 | 2.5 | 2.5 | 2.5 | 2.5 | 2.5 | 2.5 | 2.5 |
| UDMA | 15.0 | 15.0 | 15.0 | 15.0 | 15.0 | 15.0 | 15.0 |
| GDMA | 9.0 | 9.0 | 9.0 | 9.0 | 9.0 | 9.0 | 9.0 |
| MHP | 13.04 | 13.04 | 13.05 | 13.05 | 13.04 | 13.04 | 13.04 |
| Cu (II)-acetate monohydrat | 0.02 | 0.02 | 0.01 | 0.01 | 0.02 | 0.02 | 0.02 |
| CHP | 1.0 | 1.0 | — | 1.0 | — | 1.0 | — |
| AHP | — | — | 1.0 | — | — | — | — |
| TBPB | — | — | — | — | 1.0 | — | — |
| BPO | — | — | — | — | — | — | 1.0 |
| BHT | 0.01 | 0.01 | 0.01 | 0.01 | 0.01 | 0.01 | 0.01 |

TABLE 3

Summary of results of flexural strength and adhesion to dentin and enamel in the light (lc) and self-cure (sc) mode.

| | Ex. 1 | Ex. 2 | Ex. 3 | Ex. 4 | Ex. 5 | Ex. 6 | Ex. 6a |
|---|---|---|---|---|---|---|---|
| Flexural strength [MPa]; lc | 120.0 | 110.0 | 100.0 | — | 104.0 | 140.0 | 100.0 |
| Flexural strength [MPa]; sc | 105.0 | 118.0 | 100.0 | 95.0 | 83.0 | 80.0 | 100.0 |
| Adhesion to dentin [MPa]; lc | 11.2 | 10.1 | 12.2 | — | 5.6 | 10.3 | 4.1 |
| Adhesion to dentin [MPa]; sc | 13.2 | 9.4 | 12.8 | 13.4 | 8.6 | 11.8 | 4.7 |
| Adhesion to enamel [MPa]; lc | 10.1 | 7.0 | 6.3 | — | 6.6 | 14.9 | 6.3 |
| Adhesion to enamel [MPa]; sc | 9.0 | 9.7 | 8.6 | 7.1 | 5.4 | 9.2 | 4.6 |

TABLE 4

Composition of Catalyst Pastes of Example 1 (Inventive) and Examples 7-8 (Comparative)

| Component | Example 1 wt.-% | Example 7 (Thiourea instead of AA) wt.-% | Example 8 (Na-TSS instead of AA) wt.-% |
|---|---|---|---|
| Sr- glass | 62.59 | 62.00 | 60.09 |
| HDK H-2000 | 1.5 | 1.5 | 1.5 |
| UDMA | 12.68 | 13.00 | 13.00 |
| GDMA | 19.87 | 20.19 | 20.19 |
| MHP | 1.95 | 2.00 | 2.00 |
| MPDADM | 1.0 | 1.0 | 1.0 |
| CC | 0.1 | 0.1 | 0.1 |
| EDMAB | — | — | — |
| AA | 0.3 | — | — |
| AP | — | — | — |
| BHT | 0.01 | 0.01 | 0.01 |
| Thiourea | — | 0.2 | — |
| Na-TSS | — | — | 1.3 |

TABLE 5

Composition of Base pastes of Example 1 (Inventive) and Examples 7-8 (Comparative)

| Component | Example 1 wt.-% | Example 7 (Thiourea instead of AA) wt.-% | Example 8 (Na-TSS instead of AA) wt.-% |
|---|---|---|---|
| Sr- glass | 59.43 | 59.43 | 59.43 |
| HDK H-2000 | 2.5 | 2.5 | 2.5 |
| UDMA | 15.0 | 15.0 | 15.0 |
| GDMA | 9.0 | 9.0 | 9.0 |
| MHP | 13.04 | 13.04 | 13.04 |
| Cu (II)-acetate monohydrat | 0.02 | 0.02 | 0.02 |
| CHP | 1.0 | 1.0 | 1.0 |
| AHP | — | — | — |
| TBPB | — | — | — |
| BHT | 0.01 | 0.01 | 0.01 |

TABLE 6

Composition of Catalyst paste of Example 9 (Comparative)

| Component | Example 9 wt.-% |
|---|---|
| Sr- glass | 60.77 |
| Aerosil R805 | 1.49 |
| UDMA | 13.29 |
| GDMA | 21.57 |
| GDP | 1.99 |
| CC | 0.1 |
| EDMAB | 0.08 |
| AP | 0.70 |
| BHT | 0.01 |

TABLE 7

Composition of Base paste of Example 9 (Comparative)

| Component | Example 9 wt.-% |
|---|---|
| Sr- glass | 55.94 |
| Aerosil R805 | 2.48 |
| UDMA | 16.83 |
| GDMA | 9.90 |
| GDP | 13.86 |
| Cu(II)-acetate monohydrat | — |
| CHP | 0.99 |

TABLE 8

Summary of results of flexural strength and adhesion to dentin and enamel in the light (lc) and self-cure (sc) mode

| | Ex. 1 | Ex. 7 | Ex. 8 | Ex. 9 |
|---|---|---|---|---|
| Flexural strength [MPa]; lc | 120.0 | 63.0 | 117.0 | 22.0 |
| Flexural strength [MPa]; sc | 105.0 | 35.0 | 90.0 | n.a. |
| Adhesion to dentin [MPa]; lc | 11.2 | 5.1 | 8.7 | 0 |
| Adhesion to dentin [MPa]; sc | 13.2 | 0 | 4.7 | n.a. |
| Adhesion to enamel [MPa]; lc | 10.1 | 5.6 | 7.0 | 7.9 |
| Adhesion to enamel [MPa]; sc | 9.0 | 6.5 | 3.0 | n.a. | n.a.: not applicable due to no curing in self cure mode

Only the compositions obtained when mixing the compositions contained in the Base Paste and Catalyst Paste according to the present invention as described in the present text showed on the one hand sufficient mechanical properties (e.g. flexural strength) and on the other hand an improved adhesion to enamel and dentin in both the self-cure and the light-cure mode.

A composition as described in the present text but not containing a copper component was not able to self-cure and light-curing resulted in low flexural strength and no adhesion to dentin.

Compositions not containing ascorbic acid or derivative(s) thereof as reducing agent but other reducing agents (e.g. thiourea or sodium toluenesulfinate) showed insufficient performance.

It was also found that especially compositions containing an organic peroxide with an R—O—O—H moiety (hydroperoxide) showed excellent results in flexural strength and adhesion independent of curing mode.

The invention claimed is:

1. A storage-stable kit of parts for providing a curable composition, the storage-stable kit of parts comprising:

Part A comprising:
one or more of ascorbic acid, an alkali earth metal salt thereof, and an ester thereof,
polymerizable component(s) without acidic moieties,
optionally polymerizable component(s) with acidic moieties, and
filler(s);
Part B comprising:
polymerizable component(s) without acidic moieties,
polymerizable component(s) with acidic moieties,
transition metal component(s),
organic peroxide(s) selected from hydroperoxide(s) and di-peroxide(s); and
filler(s),
wherein each one of Part A and Part B is a paste and free of added water,
wherein Part A and Part B are storage stable at ambient conditions for a period of at least 4 weeks,
wherein the curable composition is self-curable,
wherein the curable composition adheres to dentin, and
a set of instructions directing a user to combine Part A and Part B to provide a cured composition.

2. The kit of parts of claim 1, the transition metal component(s) comprising Ti, V, Cr, Mn, Co, Ni, Cu, Fe, Zn, or a combination thereof, wherein the transition metal component is in hydrated or in dry form.

3. The kit of parts of claim 1, the organic peroxide(s) represented by the formula R—O—OH, wherein R is alkyl, branched alkyl, cycloalkyl, alkylaryl, or aryl.

4. The kit of parts of claim 1, the organic peroxide(s) represented by the formula $R_1$—O—O—$R_2$—O—O—$R_3$, wherein $R_1$ and $R_3$ are independently selected from H, alkyl, branched alkyl, cycloalkyl, alkylaryl or aryl; and $R_2$ is selected from alkyl or branched alkyl.

5. The kit of parts of claim 1, further comprising a photoinitiator system.

6. The kit of parts of claim 1, Part A and Part B together comprising the components in the following amounts:
one or more alkali earth metal salts of ascorbic acid from 0.01 wt.-% to 5 wt.-%;
transition metal component(s) from 0.00001 wt.-% to 3 wt.-%;
organic peroxide(s) from 0.01 wt.-% to 5 wt.-%;
filler(s) up to 90 wt.-%;
polymerizable component(s) without acidic moieties from 5 wt.-% to about 65 wt.-%; and
polymerizable component(s) with acidic moieties from 2 wt.-% to about 50 wt.-%,
wherein wt.-% is with respect to the amount of the composition.

7. The kit of parts of claim 1, not comprising one or more of the following components:
component(s) comprising a sulfinate moiety;
component(s) comprising a barbituric acid moiety;
component(s) comprising a thiobarbituric acid moiety;
component(s) comprising an aryl borate moiety; and
component(s) comprising a thiourea moiety.

8. The kit of parts of claim 1,
Part A comprising:
ascorbic acid, and
Part B comprising:
at least 4 wt % polymerizable component(s) with acidic moieties.

9. The kit of parts of claim 1, for use as anterior or posterior filling material, adhesive, cavity liner, flowable cement, coating composition, root canal filler, root canal sealant, core build-up material or a combination thereof.

10. The kit of parts of claim 1, wherein upon combined Part A and Part B produces a composition characterized by one or more of the following properties:
a) Flexural strength: at least 50 MPa determined according to according to ISO 4049:2000;
b) Adhesion to dentin: at least 5 MPa determined according to the wire loop test method; and
c) Adhesion to enamel: at least 5 MPa determined according to the wire loop test method.

11. The kit of parts of claim 1, wherein the transition metal component(s) is selected from copper acetate, copper chloride, copper benzoate, copper acetylacetonate, copper naphthenate, copper carboxylates, copper bis(1-phenylpentan-1,3-dione), copper complexes, and a combination thereof, in hydrated or in dry form.

12. The kit of parts of claim 5, the photoinitiator system comprising a sensitizer and a reducing agent.

* * * * *